(12) United States Patent
VanWiggeren et al.

(10) Patent No.: US 7,586,614 B2
(45) Date of Patent: Sep. 8, 2009

(54) SYSTEM AND METHOD FOR SELF-REFERENCED SPR MEASUREMENTS

(75) Inventors: Gregory D. VanWiggeren, San Jose, CA (US); Scott W. Corzine, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 665 days.

(21) Appl. No.: 11/210,633

(22) Filed: Aug. 24, 2005

(65) Prior Publication Data

US 2007/0046943 A1 Mar. 1, 2007

(51) Int. Cl.
G01N 21/43 (2006.01)

(52) U.S. Cl. .......................... 356/445; 436/34
(58) Field of Classification Search ............ 356/445
See application file for complete search history.

(56) References Cited

U.S. PATENT DOCUMENTS 5,991,488 A 11/1999 Salamon et al.
6,127,183 A * 10/2000 Ivarsson et al. ............. 436/34
6,734,956 B2 5/2004 Byrne et al.

OTHER PUBLICATIONS

Jung et al. "Quantitative Interpretation of the Repsonse of Surface Plasmon Resonance Sensors to Adsorbed Films", Langmuir 1998, vol. 14, pp. 5636-5648.*

Dostalek et al. "Surface plasmon resonance biosensor based on integrated optical waveguide", Sensors and Actuators B 76, 2001, pp. 8-12.*

J.H. Grassi et al., "Temperature-Dependent Refractive Index Determination from Critical Angle Measurements: Implications for Quantitative SPR Sensing," Analytical Chemistry, vol. 71, No. 19, Oct. 1, 1999, pp. 4392-4396.

J. Homola et al., "A novel multichannel surface plasmon resonance biosensor," Sensors and Actuators B, vol. 76 (2001), pp. 403-410.

M.J. O'Brien II, et al., "SPR biosensors: simultaneously removing thermal and bulk-composition effects," Biosensors & Bioelectronics, vol. 14 (1999), pp. 145-154.

K.A. Peterlinz et al., "Two-color approach for determination of thickness and dielectric constant of thin films using surface plasmon resonance spectroscopy," Optics Communications, vol. 130 (1996), pp. 260-266.

* cited by examiner

Primary Examiner—Gregory J Toatley, Jr.
Assistant Examiner—Rebecca C Slomski

(57) ABSTRACT

A system and method of using a refractive index sensor to determine a characteristic of a sample. The operation of the system and method allow for determining a change in a bulk index of the sample, and an amount of sample adsorption, using a reflected beam from an interface of the sensor. An embodiment of a system and method further provide for identifying changes in incident angles determine from reflective measurement data of the sensor, in combination with different proportionality constants of the refractive index sensor to determine a characteristic of the sample.

21 Claims, 4 Drawing Sheets

SYSTEM AND METHOD FOR SELF-REFERENCED SPR MEASUREMENTS

DESCRIPTION OF RELATED ART

Surface Plasmon Resonance (SPR) Sensors have been widely used to analyze characteristics of elements in a sample. Such sensors possess a thin conducting film situated at an interface between two optical media. When an illumination beam is incident on the interface at a particular angle satisfying certain resonance conditions the light energy input to the interface will resonantly couple with plasmon waves (comprising oscillating free electrons) at the interface. The effect of optical energy being absorbed by the oscillating electrons is observable as a decrease in the amount of energy reflected from the interface. This resonant phenomenon is called SPR.

In one embodiment, the SPR sensor will include a prism and a thin metal film affixed to one side of the prism, and on the side of the metal film which is not in contact with the prism, a binding element such as a ligand is applied. A sample is then exposed to the side of the thin metal film with the binding element, and some amount of the sample can be adsorbed on the binding element of the sensor. This adsorption of the sample element will in effect change the composition of the interface between the thin metal film and the sample to which the thin metal film is exposed. This change in the composition of the material at the interface will result in changes in the effective refractive index at the interface. These changes in the effective refractive index result in concomitant changes in the observed angle of incidence that generates an SPR.

As has been widely recognized in the past, one difficulty with SPR sensors is that it can be difficult to distinguish the bulk refractive index effects of the sample fluid, for example, from the refractive index changes due to elements of the sample being adsorbed on the binding element of the sensor. For example, the paper entitled, "SPR biosensors: simultaneously removing thermal and bulk-composition effects" by Michael J. O'Brien et al, Biosensors & Bioelectronics 14 (1999) 145-154, discusses some of the difficulties with prior SPR biosensor systems.

In operation SPR systems seek to measure the amount of material adsorbed at the surface of the sensor interface during a biochemical interaction, where this interaction is typically the binding (generally this will be referred to as adsorption) of some element in a sample with a binding element of the SPR sensor. As discussed herein the binding of some element of the sample with the binding element of the SPR is referred to as adsorption, where the element of the sample is adsorbed on the binding element. SPR sensors operate as effective refractive index sensors, and as such they operate to provide a signal which corresponds to the effective refractive index in an area near the SPR sensor surface interface. The sensed effective index depends on the amount material adsorbed on the binding element of the sensor, and it also depends on the refractive index of the sample itself. The refractive index of the sample is referred to herein as the bulk index, and this bulk index can depend on a number of factors including the actual composition of the sample and the temperature of the sample.

In order to accurately measure the amount of the element of the sample which is adsorbed at the sensor surface, an SPR system must distinguish between contributions to the effective index from adsorption and from the bulk index effects, such as those arising from changes in the temperature or composition of the sample. Many present SPR systems typically make a reference measurement in order to distinguish between adsorption effects and bulk index effects. The reference measurement typically measures the sample using a sensor interface area to which no binding element has been applied. In most instances, the sample is a fluid which is flowed across an interface area of a sensor, so one of the goals of the reference measurement is to keep the reference sample at the same temperature for both the actual adsorption measurement channel, and the reference measurement channel. A comparison of the data from the adsorption measurement channel and the reference measurement channel is then made, so that the bulk index effects measured in the reference channel can be identified, which provides a means for determining the effects of adsorption in the adsorption measurement channel.

The above type of prior art approach can be successful at eliminating some ambiguity but it has some limitations. Indeed, practical considerations involved in actually implementing dual measurement channels often limit an SPR sensor's accuracy. The necessity of a separate reference channel for the reference measurement can also limit the range of applications available to a typical SPR sensor. Additional complications also arise in the fluid systems for delivering the sample fluid to the sensor measurement areas for both the reference measurement and the actual adsorption measurement, in which it is important that the sample in both channels be simultaneously at the same temperature and of the same composition.

Other prior approaches have considered using illumination beams having different two different wavelengths to provide SPR measurements; for example, one paper entitled "Two-color approach for determination of thickness and dielectric constant of thin films using surface plasmon resonance spectroscopy", K. A. Peterlinz et al., Optics Communications 130 (1996) 260-266 describes using two wavelengths to simultaneously interrogate a sample. The signals from the two wavelengths differ in their relative response to bulk index changes and adsorption. This approach has generally not been compatible with the needs of commercial instrumentation, which require very high sensitivity, high-speed, and large dynamic range performance.

Another prior approach described in "A novel multichannel surface plasmon resonance biosensor" by Jiri Homola et al., Sensors and Actuators B 76 (2001) 403-410, provides for using two different substrates in order to measure resonances simultaneously, and then the adsorption contribution to the effective index was extracted. However, the multi-substrate approach inherently lacks sensitivity and can be difficult to easily incorporate into a highly multiplexed system.

DETAILED DESCRIPTION

As will be described in more detail herein, an embodiment of the present invention provides for determining characteristics of a sample by sensing changes in the effective refractive index at the interface of a sensor. An embodiment of a system and method described herein provides for using just a single area or a single measurement spot on a refractive index sensor to determine adsorptive characteristics of the sample.

Figure 1:
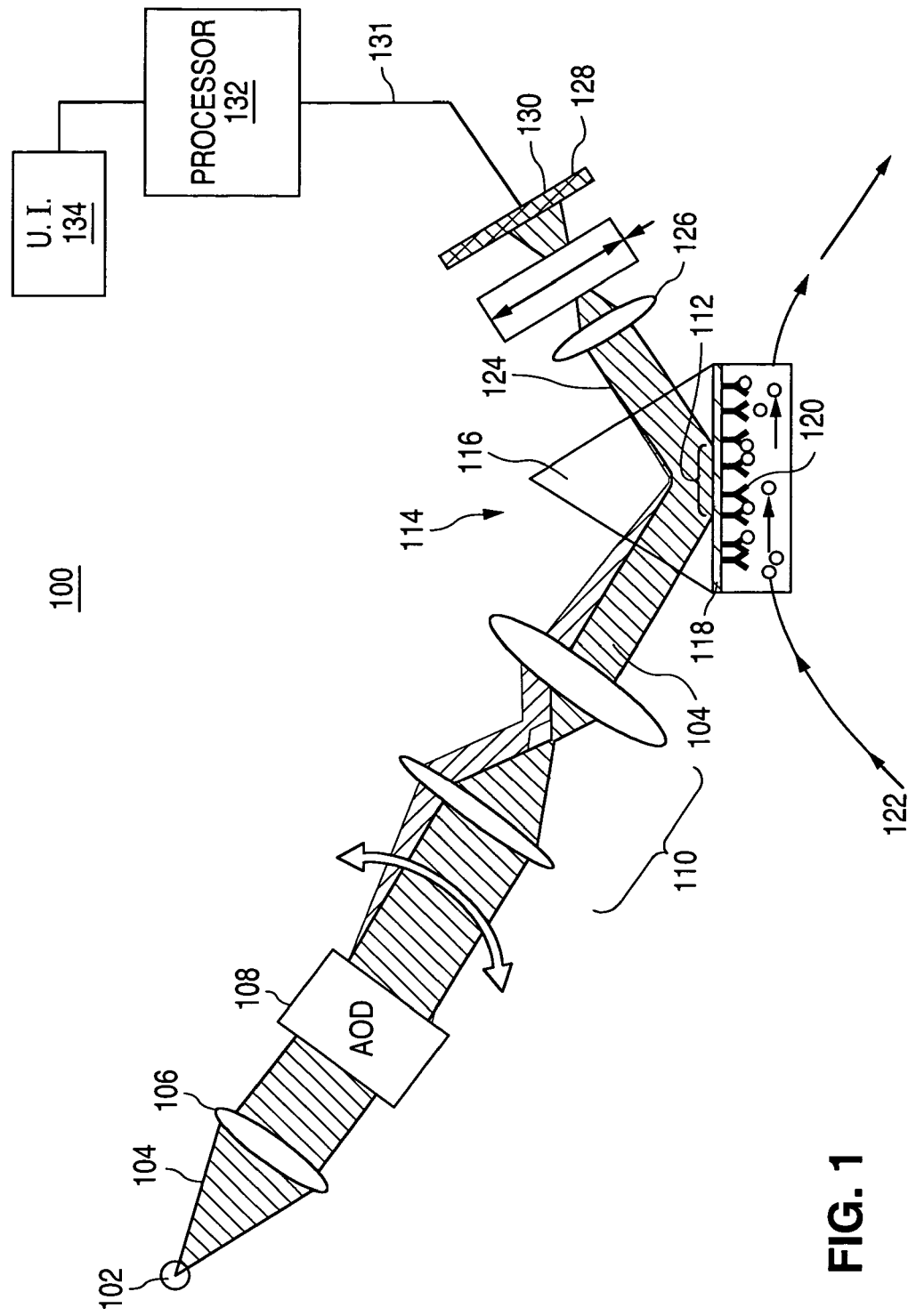
FIG. 1 shows an embodiment of a system herein.

FIG. 1 shows an embodiment of a system 100 herein. The system 100 provides for self-referenced measurements, in that it allows for using a single measurement channel to determine both the bulk index and the adsorptive contributions, whereby this single measurement channel operates as a self-referenced measurement channel. The measurement channel includes an illumination source 102 which generates an input beam 104. The illumination source can include a wide range of different electromagnetic radiation sources, such as lasers, laser diodes, or superluminescent light emitting diodes. Generally, the illumination source will output a relatively narrow bandwidth of light as the input beam. The input beam 104 is collimated by a collimation lens 106. An acousto-optic deflector 108 is then used to provide for a range of different angles for the transmission of the input beam. A telescope 110 is then used to capture the input beam across its angular range and to direct the input beam onto a measurement interface 112 of the refractive index sensor 114. In one embodiment the AOD 108 in combination with the telescope 110 will provide for an angular range of approximately 6.6 degrees for the input beam 104. The refractive index sensor 114 can be an SPR sensor which outputs an output beam 124 that corresponds to an effective index of refraction created at the interface 112 of the sensor.

In the embodiment of the system 100, the refractive index sensor includes a transmissive prism 116. A metal film 118 is coupled to one side of the prism 116, and the metal film 118 can form a sample interface area. A binding element 120 is then deposited on the side of the metal film 118 which is not in contact with the prism 116. Additionally, other embodiments could allow for a dielectric layer disposed between the metal film 118 and the ligand. This binding element can be a ligand, and a wide range of different binding elements are known in the field of SPR sensors. A sample 122 is then flowed across the sample interface area of the refractive index sensor. The sample can include a buffer fluid which conveys an element under test which is responsive to the binding element 120, such that the element under test is adsorbed on the binding element, or is in some other manner attached to the binding element such that the effective refractive index near the surface of the metal film with the binding element is altered due to some bonding between the element under test and the bonding element. In general operation of an SPR sensor the effective refractive index corresponds to the averaged refractive sensed by the evanescent tail, where the evanescent tail is an electromagnetic field sustained at the interface of the sensor, and in the immediate vicinity of the interface. In many instances the element under test is referred to as an analyte. It should also be noted that in some instances the fluid itself may be the element under test.

The input beam 104 is shown as being input to one of the sides of the prism 116, and then it is incident on the measurement interface area 112 across a range of incident angles. The input beam 104 is then reflected off of the measurement area 112, and this reflected beam is then transmitted from the refractive index sensor as an output beam 124. In the embodiment of the system 100, the output beam 124 is transmitted through an imaging lens 126, and then through a polarizer 128, and then the output beam 124 is received by an optical sensing device 130. The optical sensing device could be implemented using wide range of different optical sensors. In one embodiment, the optical sensor 130 could be a 2-D array of solid state photodetectors. The optical sensor will then output a reflectance signal 131 based on the detected output beam 124.

The system 100 further includes a processor 132 which is programmed to analyze the reflectance signal 131 to determine a characteristic of the sample. The processor could be implemented in a standard personal computer, or in a specialized measurement system. The processor could be provided with a range of different user interface devices 134, which would allow a user to input different operational parameters into the processor, and the processor could then control the operation of the measurement system. Although not shown in FIG. 1, the processor 132 could be coupled with the illumination source 102 and the AOD 108 and other elements of the system 100 to control the operation of the various elements. Further, a user interface device 134 such as a printer and or a display could be coupled with the processor to output the results of the measurements and analysis provided by the system 100.

The refractive index sensor 114 is sensitive to changes in the effective index of refraction on the sensing side of the metal film, where the sensing side is the side of the metal film which has the binding element. The effective index of refraction has contributions from both bulk index effects (temperature, concentration etc) and from adsorption effects between the sample and the binding element. In one embodiment of the system 100, the system operates to determine the change in the effective refractive index due to adsorption; thus the change in the refractive index due to the bulk index effects must be accounted for. As discussed above, in some prior systems the effect of bulk index was determined using a spatially separate reference channel. In such systems using a separate reference channel, the accuracy with which the reference channel can serve as a reference depends on its proximity to the sample channel, where the sample fluid is flowing across the binding element of the refractive index sensor. Optimally the two channels would see exactly the same fluid at exactly the same time and temperature, etc. In reality, this optimal arrangement is difficult to achieve and the displacement of the two channels serves to limit the accuracy of the absorptive measurement. This is especially true in situations where large changes in the bulk index are observed, or in situations in which there is non-specific adsorption in the reference channel.

The system 100 can use a single measurement channel, and provides for refractive index measurements that can differentiate between the bulk index and adsorption contributions to changes in the effective refractive index, without requiring two spatially separate channels (an absorptive channel and a reference channel). The operation of the system 100 provides a level of sensitivity which is comparable to prior systems. Further, certain aspects of the present invention can be practiced using prior SPR systems, where, however, the processor would be programmed to implement different methods, which are described herein for determining an amount of adsorption. Thus, a system could be used in some applications to provide for traditional two channel referencing, and in other applications a self-referencing technique as described herein could be utilized.

Figure 2:
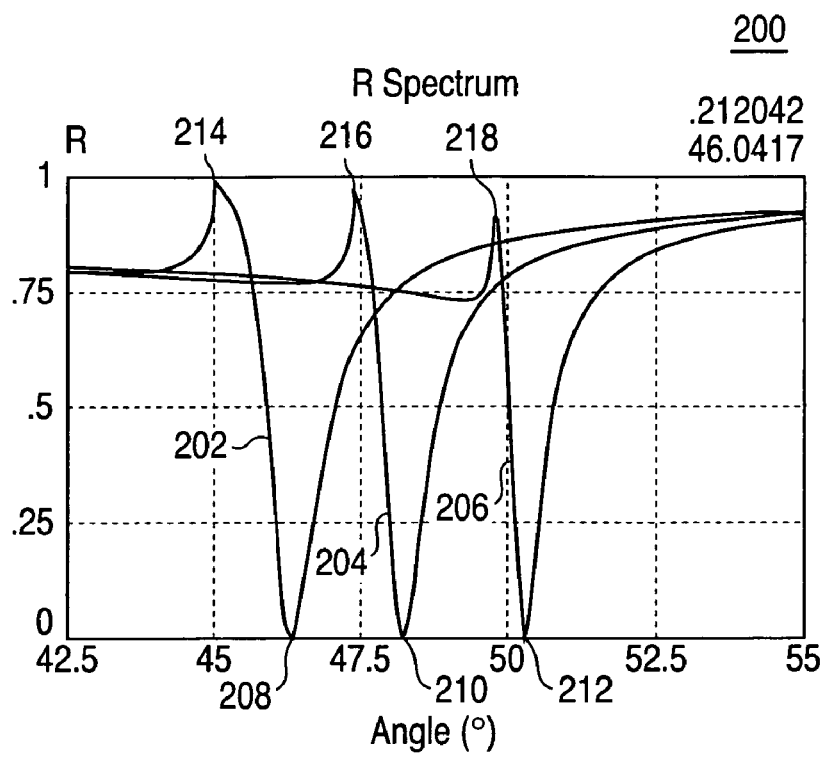
FIG. 2 shows a graph which illustrates the operation an embodiment of a system herein, and provides details used to explain a method herein.

FIG. 2 provides a graph 200 which shows reflectance measurement data for different samples being flowed through a refractive index sensor as shown in FIG. 1. In graph 200 measurement curves 202, 204 and 206 show the reflectivity versus the incident angle for three fluid samples, where the fluid corresponding to curve 202 has a refraction index of water (1.33), and the fluid corresponding to curve 204 has a refraction index of water+0.025 (1.355), and the fluid corresponding to curve 206 has a refraction index of water+0.05 (1.38). The resonance minimum points 208, 210 and 212 for each of the three curves are shifted approximately 2 degrees for each of the respective measurement curves. The maximum points 214, 216 and 218 for each of the measurement curves are shown as being approximately 1 degree less angle of incidence than the angle at which the corresponding minimum for the measurement curve occurs. The maximum points correspond to the critical angle for the total-internal-reflection. The maximum points shift to the right with increasing sample refractive index, but this shift is at a slightly different rate that the rate at which the resonant minimum point shifts to the right. The dependence on bulk index for both the minimum and the maximum can be modeled analytically or simulated numerically, or calibrated experimentally.

Figure 3:
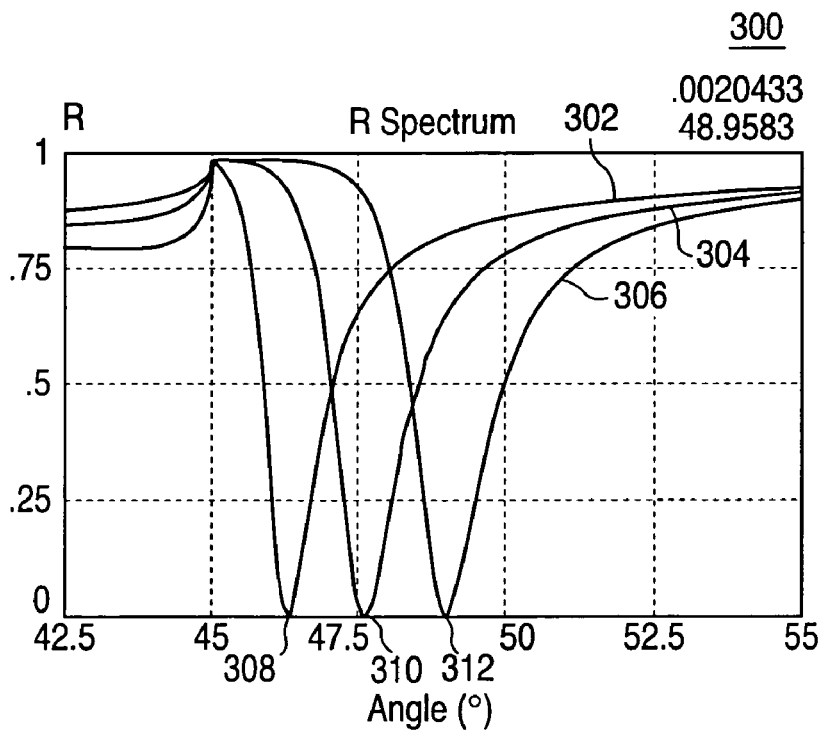
FIG. 3 shows a graph which illustrates the operation an embodiment of a system herein, and provides details used to explain a method herein.

The effect of adsorption on the measurement curve is different than the effect of a change in the bulk index on the resonance curve. FIG. 3 shows a graph 300 with three measurement curves 302, 304 and 306 where the bulk index for each of the samples for each of the curves is the same but the amount of the adsorption by the binding element of the sensor is varied to illustrate the effect of the change in adsorption on the reflectance measurements. Note that as shown in curves 302, 304 and 306, the critical angle, which in this example is also the point of maximum reflectivity, occurs at the same angle for each of the curves. However, the adsorption differences do lead to noticeable difference in the resonance minimum points 308, 310 and 312.

Figure 4:
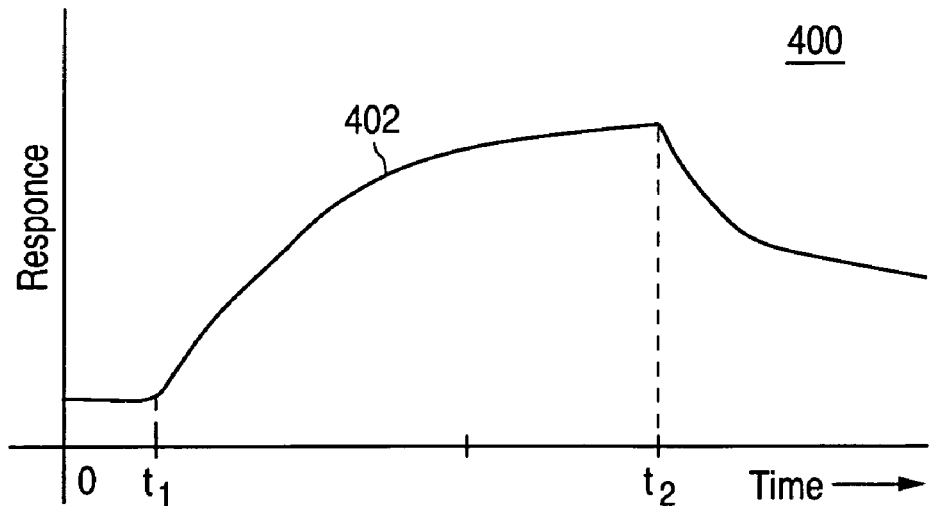
FIG. 4 shows a graph which illustrates the operation of an SPR sensor.

FIG. 4 shows a graph 400 which illustrates an aspect of the operation of an SPR system. The curve 402 shows a resonance response curve for a sample being flowed through an SPR sensor. The flowing of the sample through the sensor begins at time (t1) as the sample is flowed over the binding element of the sensor, and the element under test is adsorbed on the binding element on the metal file of the sensor. Over time more of the element under test is adsorbed on the binding element, and the resonance response signal increases in magnitude, until some maximum level of adsorption is reached, and at time t2 the flowing of the sample is stopped and the resonance response decreases as the element under test dissociates from the binding element.

In operation of the system 100, the AOD 108 operates to sweep the illumination beam across a range of angles during the time period that the sample is exposed to the binding element interface of the refractive index sensor. In one embodiment this operation of the sweeping the illumination beam operates to provide for a range of incident angles at the interface. In one embodiment the range of incident angles is approximately 6.6 degrees, with the incident angle going from a minimum of slightly less than 51 degrees to a maximum of slightly more than 57 degrees. In one example, the time period for which a sample is flowing in the refractive index sensor is about 600 seconds, and during the this time period the incident angle will be swept across a 6.6 degree range at a rate of approximately 10 Hz.

Each sweep of the illumination beam across its range of incident angles will generate a reflectance measurement curve data similar to the curves shown in graph 200, in that each sweep will provide a maximum point and a minimum point. Over the course of the time period of the sample exposure, typically both the angle of incidence for the maximum point and the minimum point will be seen to shift, as both the bulk index and the amount of adsorption will change over the course of the exposure time.

The change in the incident angle for the critical angle is given by the equation $$\Delta\Theta_1 = \frac{d\Theta_1}{dn}\bigg|\Delta n + \frac{d\Theta_1}{dx}\bigg|\Delta x$$

where $\Delta\Theta_1$ corresponds to changes in the critical angle, typically where the maximum point on the curve is;

$$\frac{d\Theta_1}{dn}$$

corresponds to sensitivity of critical angle to a change in the refractive index of the sample, where these changes in the refractive index can be due to changes in the temperature of the sample, or the composition of the sample etc., and this sensitivity value is referred to herein as a bulk index proportionality constant;

$\Delta n$ corresponds to the change in the bulk index;

$$\frac{d\Theta_1}{dx}$$

corresponds to a sensitivity of critical angle to a change in the adsorption of the element under test with the binding element of the sensor, and is referred to herein as a surface adsorption proportionality constant; and $\Delta x$ corresponds to an amount of adsorption of the sample by the binding element of the sensor.

It should be noted that bulk index proportionality constant and the surface absorption proportionality constants discussed above can be approximated as constants across a range of angles and conditions; however, the proportionality constants have higher order effects which can be accounted for using higher order terms in the above equations, or by taking into account that $$\frac{d\Theta}{dn} \text{ and } \frac{d\Theta}{dx}$$

are themselves functions on n and x. The actual values and functional dependencies for these terms can be determined using different modeling techniques, or using actual calibration type data.

As shown by the graphs 200 and 300 and the related discussion above, the change in the critical angle in the reflectance measurement data is due to changes in the bulk index; changes in the adsorption do not lead to changes in the critical angle. In one embodiment, over the course of the exposure time of the sample to the binding element of the refractive index sensor, the incident angle of the illumination beam will scanned across its range of 6.6 degrees hundreds, or possibly thousands of times. Each of these scans can then be used to produce reflectance measurement curve data. The processor of the system is programmed to identify the critical angle, typically where the maximum reflectance occurs, in a number of the reflectance measurement curves, and to determine a change in the critical angle due to a change in the bulk refractive index of the sample. This change in the critical angle corresponds to $\Delta\Theta_1$ for the above equation.

The value of the bulk index proportionality constant for a given refractive index sensor is a determinable characteristic of the refractive index sensor. This value of the bulk index proportionality constant can be determined experimentally by testing the output of the sensor using a number of samples having a known bulk index, or alternatively the design of refractive index sensors has progressed to the point where the operation of the various components can be modeled to determine a bulk index proportionality constant for a given refractive index sensor. It is also important to note that the surface adsorption proportionality constant can also be determined for a given refractive index sensor, in a manner similar to that used to determine the bulk index proportionality constant, such as by testing the sensor using different known adsorption amounts, or by modeling the response of the refractive index sensor to known adsorption amounts. Such modeling can be accomplished, for example, using the Fresnel reflectivity equations.

Given that the critical angle is not impacted by the amount of adsorption, then the above equation can be reduced to simply:

$$\Delta\Theta_1 = \frac{d\Theta_1}{dn}\bigg| \Delta n$$

where all the values except for $\Delta n$, the change in the bulk index, are known. Thus, the above equation can be solved to provide $\Delta n$, the change in the bulk index.

Having determined the change in the bulk index, a similar approach can be used to determine an amount of adsorption of the sample by the binding element of the refractive index sensor.

The same reflectance measurement curve data used by the processor of the system to identify the change in the critical angle can be used by the processor to determine the change in the angle of incidence for the resonance minimum of the measurement curves. Further the equation below can be used to determine the amount of adsorption by the binding element $$\Delta\Theta_2 = \frac{d\Theta_2}{dn}\bigg|\Delta n + \frac{d\Theta_2}{dx}\bigg|\Delta x,$$

where $\Delta\Theta_2$ corresponds to changes in the incident angle where the minimum point on the curve is, and each of the other elements of the equation generally correspond to elements described above. More specifically, $\Theta_2$ corresponds to the resonance minimum angle, and $$\frac{d\Theta_2}{dn} \text{ and } \frac{d\Theta_2}{dx}$$

are proportionality constants, which are analogous to the proportionality constants discussed above in connection with analyzing a change in the critical angle. Also, as is clear from the above discussion all of the values of the equation above are known except for the $\Delta x$. Thus, the above equation can be solved for $\Delta x$, which will provide for a measure of the amount of material adsorbed on the binding element of the sensor. Thus, using the above described system and method, one is able to determine the adsorption in the refractive index sensor in manner which does not require two separate measurement channels, or multiple wavelength measurements. This system and method utilize the bulk index proportionality constant and the surface adsorption proportionality constant of the refractive index sensor to determine the amount of adsorption using a single illumination beam and a single measurement channel.

Figure 5:
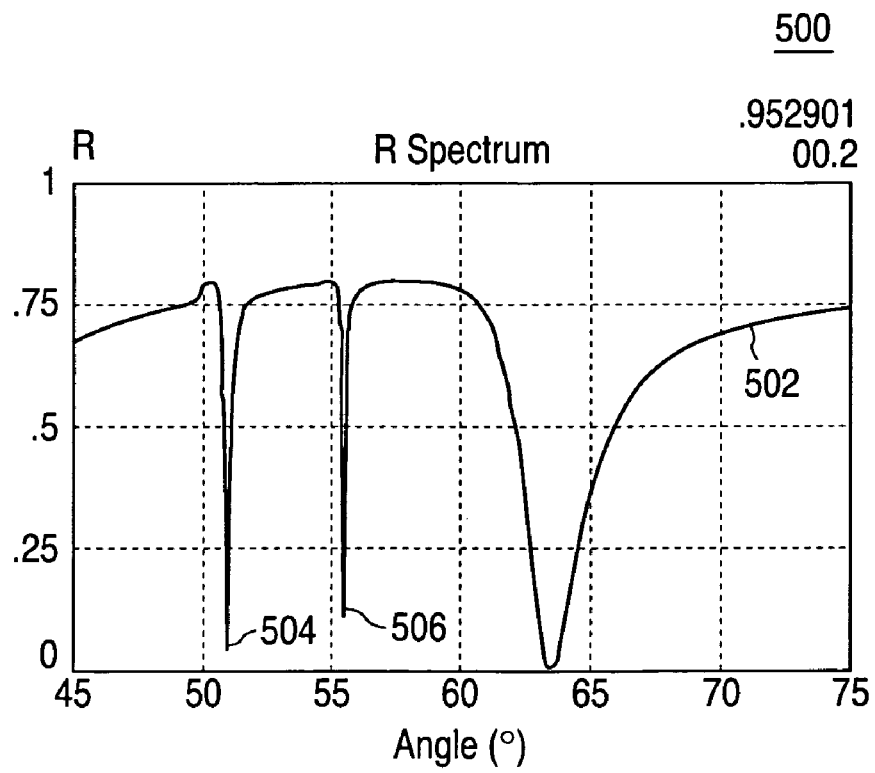
FIG. 5 shows a graph which illustrates the operation an embodiment of a system herein, and provides details used to explain a method herein.

FIG. 5 shows graph 500 which illustrates another embodiment herein. The reflectance measurement curve 502 of FIG. 5 shows two resonance minimum points 504 and 506. These two minimum points correspond to two different resonance modes at the interface where the binding element of the sensor and sample interact. The sensor corresponding to measurement curve 502 is similar to the sensor shown in FIG. 1, but in some respects it is different. Specifically, the sensor used in obtaining measurement curve 502 provides for a dielectric being disposed between the metal film and the binding element of the sensor. For example, some of the specific characteristics of the refractive index sensor corresponding to the measurement curve 502 are provided. This sensor has a metal film of gold which is approximately 325 nm thick. The prism used in the sensor is an SF18 prism, where SF18 is a reference to a specific type of high quality glass, but wide range of different qualities of glass or other materials could be used. On the side of the metal film which is opposite the prism, a first dielectric layer of $TiO_2$ is disposed, and then a second dielectric layer of the $SiO_2$ is disposed on the first dielectric layer. The first dielectric layer has a thickness of 120 nm, and the second dielectric layer has a thickness of 1800 nm. The binding element of the sensor is then disposed on the second dielectric layer, and the sample is then flowed through the sensor such that the sample is exposed to the binding element of the sensor.

During the time period that the sample is exposed to the binding element, the angle of the illumination beam is scanned in the manner described above. This scanning of the angle of incidence of the illumination beam provides for multiple measurement curves 502, where the angle of incidence for the minimum points 504 and 506 will change as the bulk index changes and as the binding element adsorbs material. As shown the minimum points correspond to two different angles of incidence ($\Theta_1$, and $\Theta_2$) and these resonance points correspond to two different modes of resonance in the refractive index sensor. These different modes at different incidence angles have different $$\frac{d\Theta}{dn} \text{ and } \frac{d\Theta}{dx}$$

values which can be modeled, or determined through experimentation for a given sensor design. For the sensor used to obtain the data shown in graph 500, the values for the proportionality constants at the first resonance point 504, are:

$\frac{d\Theta_1}{dn}$ value is $1 \times 10^{-5}$ and $\frac{d\Theta_1}{dx}$ value is .011 (degree/nm).

Further the proportionality constants for the sensor at the resonance point 506, are:

$\frac{d\Theta_2}{dn}$ value is $2 \times 10^{-6}$ and $\frac{d\Theta_2}{dx}$ value is .0035 (degree/nm).

The processor of the system is programmed to determine the change in the angle of incidence for the minimum points 504 and 506 over time, where $\Delta\Theta_1$ corresponds to the angular change for minimum point 504, and $\Delta\Theta_2$ corresponds to the angular change for minimum point 506. Using the following equations $$\Delta\Theta_1 = \frac{d\Theta_1}{dn}\bigg|\Delta n + \frac{d\Theta_1}{dx}\bigg|\Delta x$$

$$\Delta\Theta_2 = \frac{d\Theta_2}{dn}\bigg|\Delta n + \frac{d\Theta_2}{dx}\bigg|\Delta x$$

it will be observed that we have two equations with two unknowns, and thus the processor can solve the equations for $\Delta n$ and for $\Delta x$. Thus, the value of $\Delta x$, which corresponds to the adsorption of the sample element on the binding element can be determined. It should also be noted $\Delta\Theta_1$ and $\Delta\Theta_2$ could also correspond to different input beam polarizations such as S polarized light and P polarized light.

Figure 6:
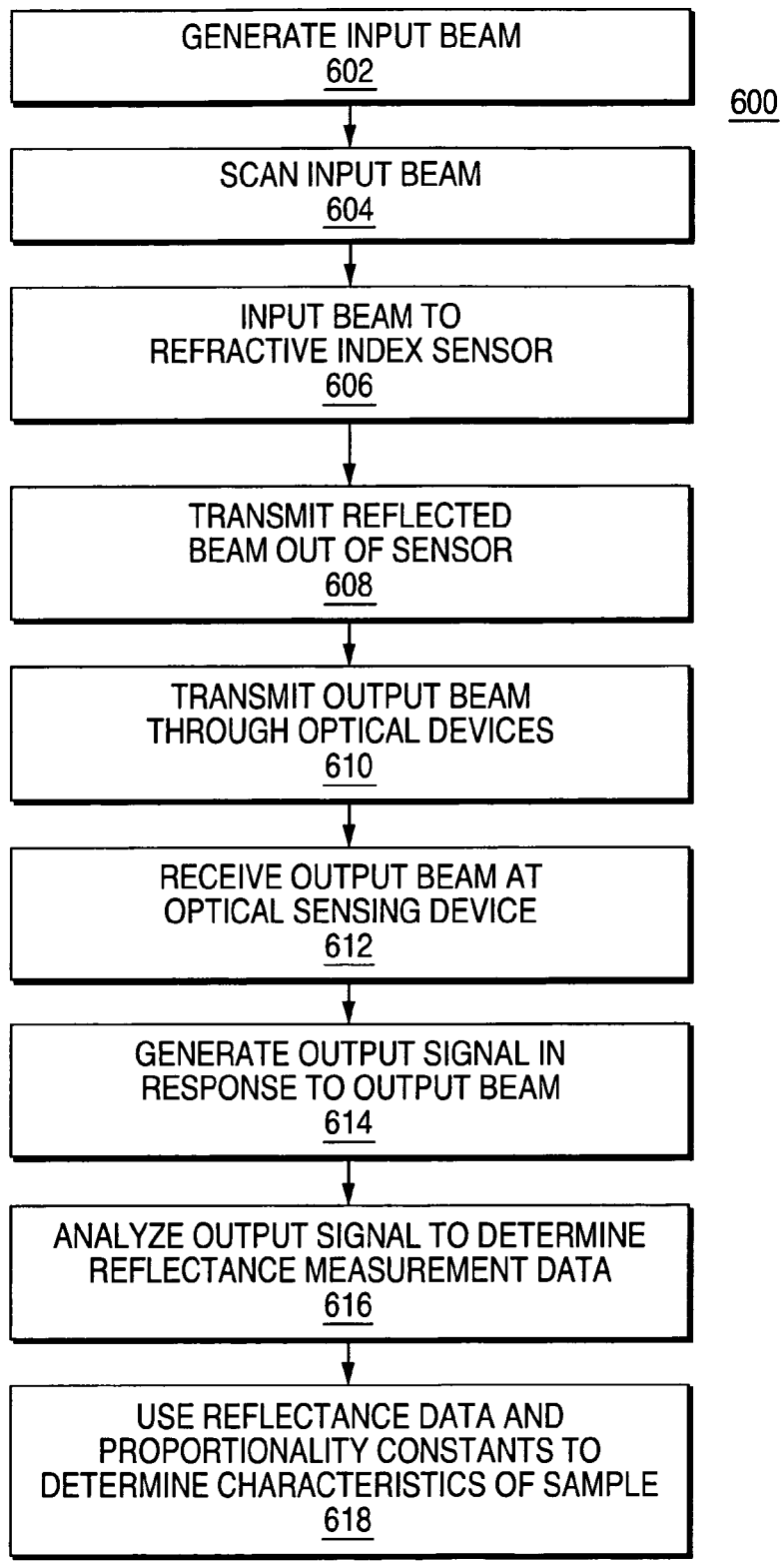
FIG. 6 shows an embodiment of a method herein.

FIG. 6 is a flow chart illustrating an embodiment 600 of a method herein. At 602 an illumination source generates an input beam. The input beam is scanned 604 through a range of angles. The input beam is then input 606 to a refractive index sensor. A sample is exposed to the refractive index sensor such that the sample is brought into contact with an interface area of the sensor, wherein the sample can interact with a binding agent at the interface, and a portion of the sample can be adsorbed on the binding agent. The input beam is incident at the interface, and beam is reflected from the interface, and transmitted 608 out of the refractive index sensor as an output beam. The output beam can then be transmitted 610 through various optical devices such as an imaging lens and a polarizer, and is then received 612 by an optical sensing device. In response to receiving the output beam, the optical sensing device generates 614 an output reflectance signal which corresponds to the output beam. The output reflectance signal is then analyzed 616 to determine reflectance measurement curve data. The reflectance measurement curve data is then used 618 in combination with proportionality constants of the refractive index sensor to determine characteristics of the sample.

One embodiment of a method herein provides for using a critical angle change and a resonance minimum angle change derived from the measurement curve data to determine characteristics of the sample. In this approach the method provides for identifying a change in the critical angle as described above. This critical angle will change over time as the bulk index of the sample changes. As described above the change in the critical angle can then be used in combination with the bulk index proportionality constant of the refractive index sensor corresponding to the critical angle to determine a change in the bulk index of the sample. This method then provides for identifying a change in a resonance minimum angle, as discussed above, and the change in the resonance minimum angle is then used in combination with the change in the bulk index of the sample, the bulk index proportionality constant corresponding to the resonance minimum for the refractive index sensor, and a surface adsorption proportionality constant corresponding to the resonance minimum for the refractive index sensor to determine a characteristic of the sample. This characteristic of the sample can be, for example, an amount of the sample which is adsorbed on the binding element of the sensor.

Another embodiment of a method herein provides for identifying two different resonant minimum points identified in reflectance measurement curve data, as described above in connection with FIG. 5. A change in the incident angle corresponding to a first resonant minimum point is then determined, and a change in the incident angle corresponding to the second resonant minimum is also determined. These changes in the incident angles are then used in combination with bulk index proportionality constants for the refractive index sensor, and surface adsorption proportionality constants for the refractive index sensor to determine characteristics of the sample, as described above.

It should be noted that the while the above discussion and analysis provide for using a change in the effective refractive index of the sensor as function of a change in the illumination beam input angle, alternative embodiments could provide for different operations which would still utilize a bulk index proportionality constant and an adsorptive proportionality constant for the sensor to provide for self referenced measurements. For example, an alternative embodiment could provide for using an illumination source which provides for sweeping the illumination input beam across a range of wavelengths. The input angle for the illumination beam would then be held at a fixed angle and the above discussed equations and principles would then be applied to a situation where the input illumination beam provides a change in wavelength, and the change in the effective refractive index as a function of the changed input wavelength would then be used in conjunction with corresponding proportionality constants of the sensor (where $d\lambda/dn$ and $d\lambda/dx$ would replace $d\theta/dn$ and $d\theta/dx$, and $\lambda$ corresponds to the wavelength of the input beam) to determine the contributions of the bulk index and the adsorptive effect on the sensed effective index of refraction.

Although only specific embodiments of the present invention are shown and described herein, the invention is not to be limited by these embodiments. Rather, the scope of the invention is to be defined by these descriptions taken together with the attached claims and their equivalents.

What is claimed is:

1. A measurement system having a self-referenced measurement channel for analyzing a characteristic of a sample, the system comprising:

an illumination source, which generates an input beam;
a refractive index sensor which receives the input beam, and transmits an output beam, wherein the refractive index sensor includes an interface where an element of the sample is adsorbed on a binding element of the refractive index sensor, wherein the interface provides a measurement spot which receives the input beam and reflects a portion of the input beam as the output beam, and wherein the refractive index sensor has a bulk index proportionality constant;

an optical energy sensor which receives the output beam and generates an output signal; and a processor which receives the output signal, wherein the processor uses the output signal and the bulk index proportionality constant of the refractive index sensor to determine an amount corresponding to adsorption on the binding element.

2. The system of claim 1, further including wherein the processor determines a change in the bulk index.

3. The system of claim 2, further including: an angle scanning device which operates to scan the input beam across a range of incident-angles for input into the refractive index sensor.

4. The system of claim 2, further including:
wherein the refractive index sensor has a surface adsorption proportionality constant; and
wherein the processor uses the output signal, and the bulk index proportionality constant of the refractive index sensor, and the surface adsorption proportionality constant to determine an amount of the element of the sample which is adsorbed on the binding element of the refractive index sensor.

5. The system of claim 2, further including:
wherein the output signal provides reflectance measurement curve data at a plurality of different time intervals when the sample is exposed to the binding element; and
wherein the processor analyzes the reflectance measurement curve data to identify a change in a critical angle, and uses the change in the critical angle and the bulk index proportionality constant to determine a change in the bulk index of the sample.

6. The system of claim 5, further including:
wherein the processor analyzes the reflectance measurement curve data to identify a change in an incident angle for resonance minimum point in the reflectance measurement curve data, and uses the change in the bulk index of the sample, and the bulk index proportionality constant, and a surface adsorption proportionality constant of the refractive index sensor, to determine the amount corresponding to adsorption on the binding element.

7. The system of claim 2, further including:
wherein the output signal provides reflectance measurement curve data at a plurality of different time intervals; and
wherein the processor analyzes the reflectance measurement curve data to identify a first change in a first incident angle corresponding to a first resonant minimum point in the reflectance measurement curve data, and to identify a second change in a second incident angle corresponding to a second resonant minimum point in the reflectance measurement curve data, and the processor uses the first change in the first incident angle, and the second change in the second incident angle, in combination with the bulk index proportionality constant to determine the amount corresponding to adsorption on the binding element.

8. The system of claim 2, further including:
wherein the output signal provides reflectance measurement curve data at a plurality of different time intervals; and
wherein the processor analyzes the reflectance measurement curve data to identify a first change in a first incident angle corresponding to a first resonant minimum point in the reflectance measurement curve data, and to identify a second change in a second incident angle corresponding to a second resonant minimum point in the reflectance measurement curve data, and the processor uses the first change in the first incident angle, and the second change in the second incident angle, in combination with the bulk index proportionality, and a surface adsorption proportionality constant for the refractive index sensor to determine amount corresponding to adsorption on the binding element.

9. The system of the claim 2, further including:
wherein the refractive index sensor includes a prism which has a first side which receives the input beam, and the prism includes a second side on which a metal film is disposed, and the prism includes a third side which transmits the output beam to the optical energy sensor, and the binding element is disposed on a side of the metal film which is exposed to the sample.

10. The system of the claim 2, further including:
wherein the refractive index sensor includes a prism which has a first side which receives the input beam, and the prism includes a second side on which a metal film is disposed, and the prism includes a third side which transmits the output beam to the optical energy sensor; and
wherein a dielectric layer is disposed between binding element and the metal film.

11. The system of claim 2, wherein the illumination source operates to scan across a range of wavelengths for the input beam.

12. In a measurement system having a self-referenced measurement channel for analyzing a characteristic of a sample, a method comprising:
providing a refractive index sensor having an interface which adsorbs an element of a sample, and provides a measurement spot;
inputting an illumination beam to the refractive index sensor;
directing the illumination beam to the measurement spot, wherein the illumination beam is incident on the measurement spot, and a portion of the measurement beam is reflected from the measurement spot as an output beam;
transmitting the output beam from the refractive index sensor;
providing an optical energy sensor which receives the output beam, and generates an output signal which corresponds to the output beam; and
using the output signal and a bulk index proportionality constant of the refractive index sensor to determine an amount corresponding to adsorption on the binding element, and to determine a change in a bulk index.

13. The method of claim 12, further including:
scanning the illumination beam across a range of incident angles for input into the refractive index sensor.

14. The method of claim 12, further including:
using the output signal and the bulk index proportionality constant of the refractive index sensor, and a surface adsorption proportionality constant for the refractive index sensor to determine the amount corresponding to adsorption on the binding element.

15. The method of claim 12, further including:
identifying a change in a critical angle which corresponds to a maximum reflection point; and
using the critical angle and the bulk index proportionality constant to determine a change in the bulk index of the sample.

16. The method of claim 15, further including:

identifying a change in an incident angle for a resonance minimum point in the output signal, and using the change in the bulk index of the sample, and the bulk index proportionality constant, and a surface adsorption proportionality constant of the refractive index sensor, to determine the amount corresponding to adsorption on the binding element.

17. The method of claim 12, further including:

analyzing the output signal to determine reflectance measurement curve data at a plurality of different time intervals; and using the reflectance measurement curve data to identify a first change in a first incident angle corresponding to a first resonant minimum point in the reflectance measurement curve data, and to identify a second change in a second incident angle corresponding to a second resonant minimum point in the reflectance measurement curve data, and using the first change in the first incident angle, and the second change in the second incident angle, in combination with the bulk index proportionality constant to determine the amount corresponding to adsorption on the binding element.

18. The method of claim 12, further including:

analyzing the output signal to determine reflectance measurement curve data at a plurality of different time intervals; and using the reflectance measurement curve data to identify a first change in a first incident angle corresponding to a first resonant minimum point in the reflectance measurement curve data, and to identify a second change in a second incident angle corresponding to a second resonant minimum point in the reflectance measurement curve data, and using the first change in the first incident angle, and the second change in the second incident angle, in combination with the bulk index proportionality constant, and a surface adsorption proportionality constant for the refractive index sensor to determine the amount corresponding to adsorption on the binding element.

19. In a measurement system having a self-referenced measurement channel for analyzing a characteristic of a sample, a method comprising:

inputting an illumination beam into a refractive index sensor; and transmitting an output beam from the refractive index sensor, wherein the output beam includes a portion of the illumination beam reflected from an interface of the refractive index sensor, wherein the sample is in contact with the interface of the refractive index sensor;

analyzing the output signal to determine change in an angle corresponding to resonance minimum point in the output signal; and using the change in the angle corresponding to a resonance minimum point and a surface adsorption proportionality constant to determine a change in a bulk index, and to determine an amount of adsorption at the interface.

20. In a measurement system for analyzing a characteristic of a sample, a method comprising:

inputting an illumination beam into a refractive index sensor; and transmitting an output beam from the refractive index sensor, wherein the output beam includes a portion of the illumination beam reflected from an interface of the refractive index sensor, wherein the sample is in contact with the interface of the refractive index sensor;

generating an output signal corresponding to the output beam;

analyzing the output signal to determine a change in a first angle corresponding to a first resonance minimum point in the output signal;

analyzing the output signal to determine a change in a second angle corresponding to a second resonance minimum point in the output signal; and using the change in the first angle and using the change in second angle to determine an amount of adsorption on the binding element and using the change in the first angle and using the change in the second angle to determine a change in the bulk index.

21. In a measurement system for analyzing a characteristic of a sample, a method comprising:

inputting an illumination beam into a refractive index sensor; and transmitting an output beam from the refractive index sensor, wherein the output beam includes a portion of the illumination beam reflected from an interface of the refractive index sensor, wherein the sample is in contact with the interface of the refractive index sensor;

generating an output signal corresponding the output beam;

analyzing the output signal to determine a change in a first angle corresponding to a resonance minimum point in the output signal;

analyzing the output signal to determine a change in a second angle corresponding to a critical angle in the output signal; and using the change in the first angle and using the change in second angle to determine an amount of adsorption on the binding element and using the change in the first angle and using the change in the second angle to determine a change in the bulk index.

* * * * *